US009303985B2

(12) United States Patent
Zhao et al.

(10) Patent No.: US 9,303,985 B2
(45) Date of Patent: Apr. 5, 2016

(54) SYSTEM AND METHOD FOR CONTROLLING SCANNING PLANES OF IMAGING DEVICE

(75) Inventors: Lei Zhao, Hebei (CN); Wei Wei, Hebei (CN); Huagen Liu, Hebei (CN)

(73) Assignee: Symbow Medical Technology Co., Ltd. (CN)

( * ) Notice: Subject to any disclaimer, the term of this patent is extended or adjusted under 35 U.S.C. 154(b) by 841 days.

(21) Appl. No.: 13/636,545

(22) PCT Filed: Jun. 25, 2010

(86) PCT No.: PCT/CN2010/000952
§ 371 (c)(1),
(2), (4) Date: Jan. 2, 2013

(87) PCT Pub. No.: WO2011/116509
PCT Pub. Date: Sep. 29, 2011

(65) Prior Publication Data
US 2013/0132024 A1 May 23, 2013

(30) Foreign Application Priority Data
Mar. 22, 2010 (CN) .......................... 2010 1 0130676

(51) Int. Cl.
*G01C 5/00* (2006.01)
*G06F 17/00* (2006.01)
(Continued)

(52) U.S. Cl.
CPC . *G01C 5/00* (2013.01); *A61B 6/035* (2013.01); *A61B 7/003* (2013.01); *A61B 17/00* (2013.01);
(Continued)

(58) Field of Classification Search
CPC .................. A61B 17/00; A61B 19/52; A61B 2017/00207; A61B 2019/5255; A61B 6/035; A61B 6/12; A61B 7/003; A61B 8/0841; A61B 5/06; G01C 5/00; G06F 17/00
USPC ..................... 702/94, 95, 150, 152, 153, 155; 600/410, 424
See application file for complete search history.

(56) References Cited

U.S. PATENT DOCUMENTS 6,314,310 B1    11/2001 Ben-Haim et al.
6,516,213 B1 *   2/2003 Nevo ........................ A61B 5/06
                                                                600/410

FOREIGN PATENT DOCUMENTS

CN     1185935 A    7/1998
CN   101019765 A    8/2007
(Continued)

OTHER PUBLICATIONS

"International Application Serial No. PCT/CN2010/000952, International Search Report mailed Dec. 30, 2010", 5 pgs.

*Primary Examiner* — John H Le
(74) *Attorney, Agent, or Firm* — Schwegman Lundberg & Woessner, P.A.

(57) ABSTRACT

This patent indicates a type of system and method for controlling scanning planes of imaging device, it includes: tracer, on which a tracer coordinate system is built, is fixed on the target which is to be scanned; a tracking device, on which a tracking device coordinate system is built, is used to get the position and orientation of the tracer in the tracking device coordinate system and convert the known position and orientation of the target which is to be scanned from the tracer coordinate system to the tracking device coordinate system; an imaging device, on which an imaging device coordinate system is built, is used to scan the position and orientation of the said target to be scanned in the imaging device coordinate system to form images; a conversion module, which is preset in the tracking device or the imaging device, is used to convert the position and orientation of the target which is to be scanned from the tracking device coordinate system to the imaging device coordinate system; when the conversion module is preset in the tracking device, the tracking device transfers the position and orientation of the target which is to be scanned in the tracking device coordinate system to the imaging device. This patent has the ability to provide high efficiency, and high precision when scanning target image, it can be used at any type of image devices.

10 Claims, 3 Drawing Sheets

(51) Int. Cl.
 *A61B 6/03* (2006.01)
 *A61B 17/00* (2006.01)
 *A61B 19/00* (2006.01)
 *A61B 7/00* (2006.01)
 *A61B 6/12* (2006.01)
 *A61B 8/08* (2006.01)

(52) U.S. Cl.
 CPC ............... *A61B 19/52* (2013.01); *G06F 17/00* (2013.01); *A61B 6/12* (2013.01); *A61B 8/0841* (2013.01); *A61B 2017/00207* (2013.01); *A61B 2019/5255* (2013.01)

(56) References Cited

FOREIGN PATENT DOCUMENTS

| | | |
|---|---|---|
| CN | 101019771 A | 8/2007 |
| CN | 101108140 A | 1/2008 |
| JP | 9-247658 A | 9/1997 |

* cited by examiner

SYSTEM AND METHOD FOR CONTROLLING SCANNING PLANES OF IMAGING DEVICE

RELATED APPLICATIONS

This application is a nationalization under 35 U.S.C. 371 of PCT/CN2010/000952, filed Jun. 25, 2010, and published as WO 2011/116509 A1, on Sep. 29, 2011, which claims priority to Chinese patent Application Serial No. 201010130676.4, filed Mar. 22, 2010, which applications and publications are incorporated herein by reference in their entirety.

BACKGROUND OF THE INVENTION

1. Field of this Invention

This invention relates to a imaging technology, especially a system and a method for controlling scanning planes of imaging device.

2. Description of the Related Art

In some imaging devices (such as magnetic resonance, CT and PET-CT) with traditional scanning operation, in order to completely scan a target, the scan plane will need to pass that target accurately. Therefore, an general method comprises following steps: scanning one group or two groups of scout images so as to obtain part of the image of the target through the scout images; then defining the position and orientation data of target through part of the image (the position and orientation can be decomposed into three dimensions that are perpendicular to each other) in order to establish its necessary scan plane, which allows the scan plane to pass that target accurately, so as to accurately define the target. Taking a needle shaped device as an example, firstly, a group of planes that are at a certain angle with the needle shaped device to scan the device. (Referring to FIG. 1) to obtain a series of scout images. Each plane of the scout image obtained may appear as a cross section image of a needle shaped device in the form of a point. And then a scan plane 5 is established according to the points on the cross section image (referring to FIG. 2), after that the scan plane passes through those points, so that the image of the needle shaped device can be completely shown on one picture. IF the scout image 6 obtained can not well illustrate partial image of the target to be scanned, the operator may repeatedly scan the scout image until obtaining partial image of the target to be scanned which is recognizable, and then the operator scans the target to be scanned, however, the method may cause a low efficiency of scanning operation.

SUMMARY OF THE INVENTION

In view of the above-described problem, it is one object of the invention to provide a system and a method for controlling scanning planes of imaging device, which may scan a target to obtain its image with high efficiency and high precision at real time.

To achieve the above objective, in accordance with one embodiment of the invention provided is a system for controlling scanning planes of imaging device, comprising:

- a tracer, on which a tracer coordinate system is built, fixed on a target which is to be scanned;
- a tracking device, on which a tracking device coordinate system is built, for obtaining the position and orientation of the tracer in said tracking device coordinate system and converting the known position and orientation of the target to be scanned from a coordinate system of said tracer to a coordinate system of said tracking device; and
- an imaging device, for scanning the position and orientation of the target to be scanned in said coordinate system of said imaging device to form images, on which an imaging device coordinate system is built;

wherein, said tracking device or said imaging device has a conversion module preset therein, which is for converting the position and orientation of the target to be scanned from the tracking device coordinate system to the imaging device coordinate system; and when the conversion module is preset in the tracking device, the tracking device transfers the position and orientation of the target to be scanned in the tracking device coordinate system to the imaging device.

In a class of this embodiment, the expression of the conversion module $C_{track}^{scan}$ that is mentioned above is presented as:

$$C_{track}^{scan} = \begin{pmatrix} R_{track}^{scan} & T_{track}^{scan} \\ 0 & 1 \end{pmatrix}$$

wherein, $C_{track}^{scan}$ is a 4*4 matrix, $R_{track}^{scan}$ is a 3*3 rotation matrix, and $T_{track}^{scan}$ is a 3 dimensional translation vector.

In a class of this embodiment, the tracer comprises a position/orientation sensor and a fixing support. The position/orientation sensor is fixed via the fixing support on the target to be scanned. The position and orientation of the position/orientation sensor is the same as the position and orientation of the tracer.

In a class of this embodiment, the expression of the position and orientation $C_{tool}^{track}$ of the tracer in the tracking device coordinate system is presented as:

$$C_{tool}^{track} = \begin{pmatrix} R_{tool}^{track} & T_{tool}^{track} \\ 0 & 1 \end{pmatrix}$$

wherein, $C_{tool}^{track}$ is a 4*4 matrix, $R_{track}^{scan}$ is a 3*3 rotation matrix, and $T_{track}^{scan}$ is a 3 dimensional translation vector.

The invention further provides a method for controlling scanning planes of imaging device comprise steps of:

step 1: building a systems comprising a tracer, a tracking device, and an imaging device; and then fixing the tracer a target which is to be scanned; and, presetting a conversion module between a tracking device coordinate system and an imaging device coordinate system in a tracking device or an imaging device;

step 2: defining a plane through which the imaging device scans the target to be scanned as a scanning plane G, and the expression of the scanning plane G in the tracer coordinate system is presented as:

$$\vec{n}^{tool} \cdot (X^{tool} - S^{tool}) = 0$$

Wherein, $X^{tool}$ represents the coordinate of any point on the scanning plane G in the tracer coordinate system, which is a 3 dimensional vector; $\vec{n}^{tool}$ represents a normal vector for the scanning plane G in the tracer coordinate system, which is a normalized 3 dimensional vector; and $S^{tool}$ represents the coordinate of a known point on the scanning plane G in the tracer coordinate system, which is also a 3 dimensional vector;

step 3: measuring a position and orientation $C_{tool}^{track}$ of the tracer in the tracking device coordinate system 'track' with the tracking device;

step 4: calculating a first plane equation of scanning plane G in the tracking device coordinate system with the tracking device using the position and orientation $C_{tool}^{track}$ of step 3, the expression of which is presented as bellow:

$$\vec{n}^{track} \cdot (X^{track} - S^{track}) = 0$$

$$\vec{n}^{track} = R_{tool}^{track} \cdot \vec{n}^{tool}$$

$$S^{track} = R_{tool}^{track} \cdot S^{tool} + T_{tool}^{track}$$

wherein, $\vec{n}^{track}$ represents a normal vector of the scanning plane G in the tracking device coordinate system, which is a normalized 3 dimensional vector; $X^{track}$ represents a coordinate of any point on the scanning plane G in the tracking device coordinate system, which is a 3 dimensional vector; and $S^{track}$ represents a coordinate of a known point on the scanning plane G in the tracking device coordinate system, which is a 3 dimensional vector;

step 5: calculating a second plane equation of the scanning plane G in the imaging device coordinate system in terms of a conversion module $C_{track}^{scan}$ for conversion between the tracking device coordinate system and the imaging device coordinate system, wherein, an expression of the second plane equation is presented as bellow:

$$\vec{n}^{scan} \cdot (X^{scan} - S^{scan}) = 0$$

$$\vec{n}^{scan} = R_{track}^{scan} \cdot \vec{n}^{track} = R_{track}^{scan} \cdot R_{tool}^{track} \cdot \vec{n}^{tool}$$

$$S^{scan} = R_{track}^{scan} \cdot S^{track} + T_{track}^{scan} = R_{track}^{scan} \cdot (R_{tool}^{track} \cdot S^{tool} \cdot T_{tool}^{track}) + T_{track}^{tool}$$

and $\vec{n}^{scan}$ represents a normal vector of the scanning plane G in the imaging device coordinate system, which is a normalized 3 dimensional vector; $X^{scan}$ represent a coordinate of any point on the scanning plane G in the imaging device coordinate system, which is a 3 dimensional vector; $S^{scan}$ represents a coordinate of a known point on the scanning plane G in the imaging device coordinate system, which is a 3 dimensional vector; and Step 6: scanning the target to be scanned with the imaging device 3, in terms of second plane equation calculated in step 5.

an expression of the conversion matrix $C_{track}^{scan}$ in step 1 is $$C_{track}^{scan} = \begin{pmatrix} R_{track}^{scan} & T_{track}^{scan} \\ 0 & 1 \end{pmatrix}$$

wherein, $C_{track}^{scan}$ is a 4*4 matrix, $R_{track}^{scan}$ is a 3*3 rotation matrix, and $T_{track}^{scan}$ is 3 dimensional translation vector.

an expression of the position and orientation $C_{tool}^{track}$ in step 3 is $$C_{tool}^{track} = \begin{pmatrix} R_{tool}^{track} & T_{tool}^{track} \\ 0 & 1 \end{pmatrix}$$

wherein, $C_{tool}^{track}$ is a 4*4 matrix, $R_{tool}^{track}$ is a 3*3 matrix, and $T_{tool}^{track}$ is a 3 dimensional translation vector.

For step 5, the conversion module is preset in the tracking device, and the second plane equation of the scanning plane G in the imaging device coordinate system is calculated by the tracking device and then transferred to the imaging device.

For step 5, the conversion module is preset in the imaging device, and the second plane equation of the scanning plane G in the imaging device coordinate system is calculated by the imaging device.

This invention has the following advantages:

1) the system in this invention comprises a tracer, a tracking device and an imaging device and defines the coordinate systems of the tracer, the tracking device and the image device respectively as the coordinate systems built upon the tracer, the tracking device and the image device, and the tracer is fixed on a target to be scanned (such as instruments and focus etc), to allow the tracer to move with the target to be scanned, which allows the system of the invention to measure the precise position and orientation of the tracer at real time via the tracking device. It is also possible for the system of the invention to obtain the precise position and orientation of the target to be scanned in the tracking system at real time, in terms of the position and orientation of the tracer measured at real time, the known position and orientation of the target to be scanned in the tracer coordinate system, and the conversion relation between the tracking device coordinate system and the tracer coordinate system. And then it is further possible for the system of the invention to obtain the precise position and orientation of the target to be scanned in the imaging device coordinate system, in terms of the preset conversion relation between the tracking device coordinate system and the imaging device coordinate system, which may reduce error rate made due to manual operation such as manual setting of the position and orientation of the scout image. In addition, an instrument can be used as a scanning probe adapted for scanning what it points to, which may improve the operating flexibility.

2) Due to the fact that this system has preset a conversion module between the tracking device coordinate system and the imaging device coordinate system in the tracking device or the imaging device, the position and orientation of target can be converted from the tracking device coordinate system to the imaging device coordinate system at real time, so as to reduce operating time and improve imaging speed. Consequently, the system of the invention to be of high imaging speed and high imaging precision and may be applied to various imaging devices.

BRIEF DESCRIPTION OF THE DRAWINGS

Detailed description will be given below in conjunction with accompanying drawings.

DETAILED DESCRIPTION OF THE EMBODIMENTS

Figure 1:
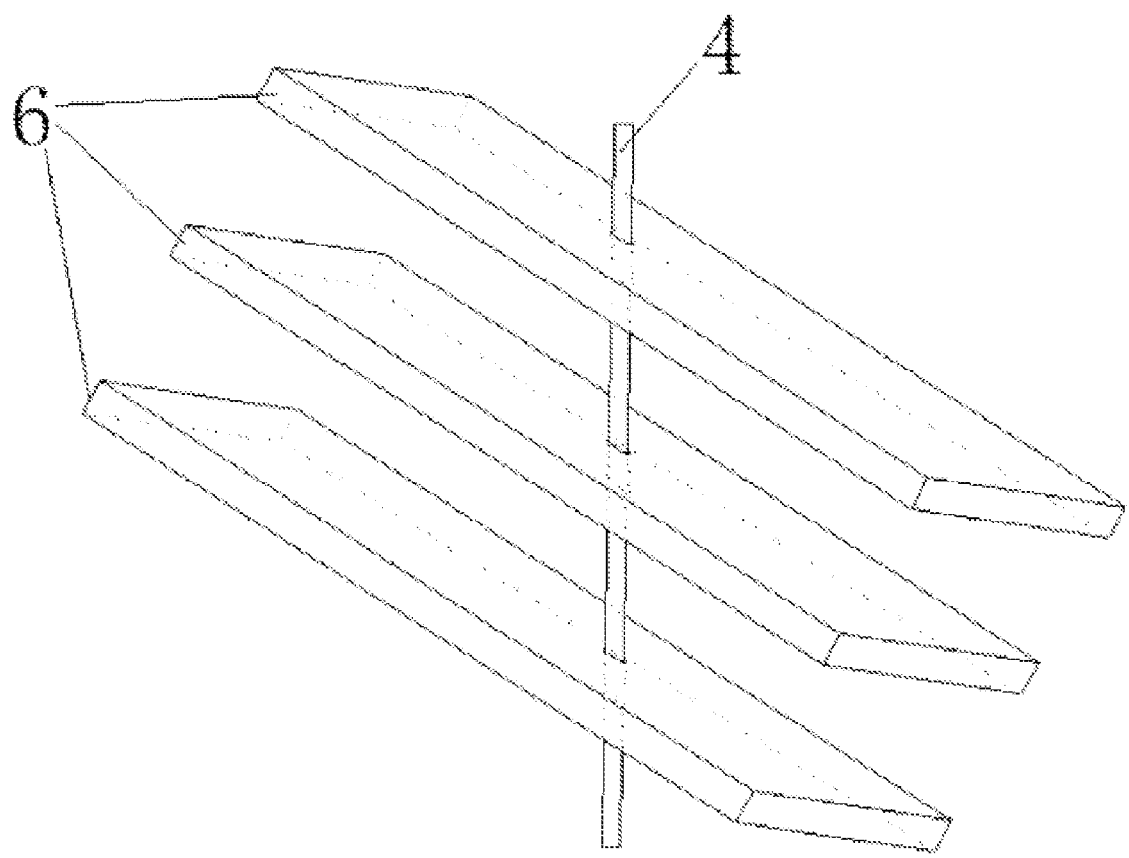
FIG. 1 shows a position image in the existing technology.
Figure 2:
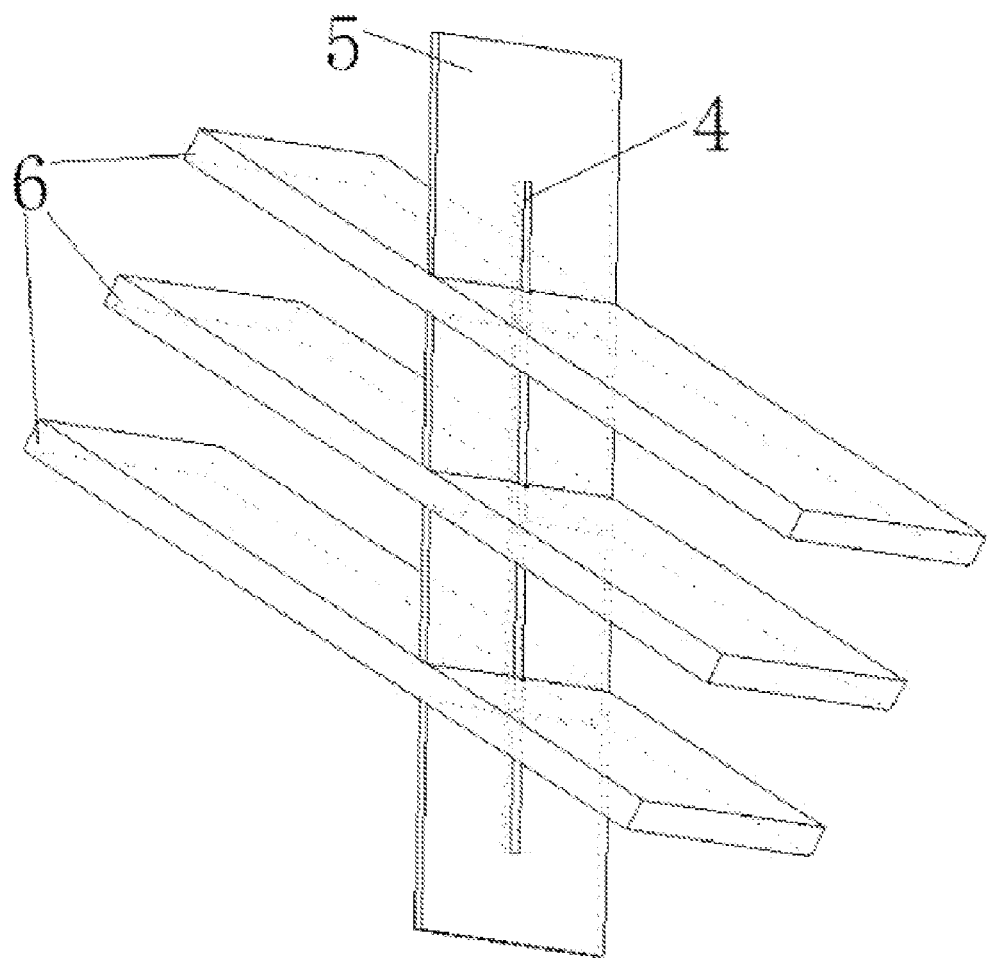
FIG. 2 shows the building of a scanning plane in the existing technology.
Figure 3:
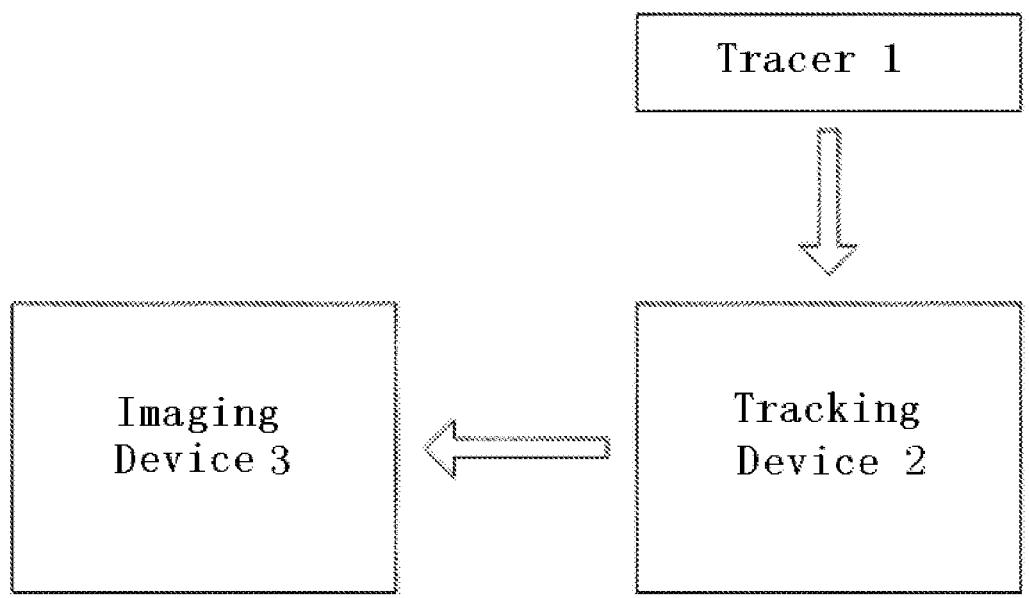
FIG. 3 shows the structure of the system of this invention.

Referring to FIG. 3, the system of one embodiment of the invention comprises a tracer 1, a tracking device 2, and an imaging device 3. For each device, a corresponding coordinate system is built thereon. Those coordinate systems can be presented as 'tool' for the tracer coordinate system, 'track' for the tracking device coordinate system, and 'scan' for the imaging device coordinate system.

The tracer 1 of one embodiment of this invention comprises a position/orientation sensor and a fixing support. The position/orientation sensor is fixed on the target (such as instruments and focus etc) which is to be scanned through the fixing support. In the tracer coordinate system 'tool', the position and orientation for the position/orientation sensor can be regarded as the position and orientation of the tracer 1. The position/orientation sensor may comprise three plastic balls with phosphor powder coating on the external surface thereof, which are not arranged in line. Tracking device 2 comprises an optical camera based on binocular vision, a computer and software. Tracking device 2 can measure the position and orientation of a position/orientation sensor. Therefore, the tracking device 2 may obtain the position and orientation $C_{tool}^{track}$ of the tracer 1 in the tracking device coordinate system 'track' by tracking and measuring the position and orientation of the position/orientation sensor of the tracer 1, which is a conversion matrix for converting a coordinate to the tracking device coordinate system 'track' from the tracer coordinate system 'tool', and an expression of the conversion matrix is presented as:

$$C_{tool}^{track} = \begin{pmatrix} R_{tool}^{track} & T_{tool}^{track} \\ 0 & 1 \end{pmatrix} \quad (1)$$

wherein, $C_{tool}^{track}$ is a 4*4 matrix, $R_{tool}^{track}$ is a 3*3 rotation matrix, and $T_{tool}^{track}$ a 3*1 matrix, which is a 3 dimensional translation vector. The subscript of $C_{tool}^{track}$, $R_{tool}^{track}$ and $T_{tool}^{track}$ is 'tool', and the superscript is 'track', which represents that the position and orientation of these variable can be converted from the tracer coordinate system 'tool' to the tracking device coordinate system 'track'.

For example, by using the formula below, a coordinate $Q^{tool}$ of any point Q in the tracer coordinate system can be converted into a coordinate $Q^{track}$ in the tracking device coordinate system track, wherein, for example, the coordinate $Q^{tool}$ can be 3 dimensional vector represented by a 3*1 matrix and the superscript 'tool' represents the coordinate is in the tracer coordinate system 'tool'; and the coordinate $Q^{track}$ can be a 3 dimensional vector represented by a 3*1 matrix, and its superscript 'track' represents the coordinate is in the tracking coordinate system 'track', the expression of the formula is presented as bellow:

$$Q^{track} = C_{tool}^{track} Q^{tool} \quad (2)$$

A certain orientation $\vec{t}$ in the tracer coordinate system 'tool' can be represented by a unit vector $\vec{t}^{tool}$ (which is a normalized 3 dimensional vector represented by a 3*1 matrix, and its superscript 'tool' represents the vector is in the tracer coordinate system 'tool'), and the orientation is converted into a unit vector $\vec{t}^{track}$ in the tracking device coordinate system 'track', wherein, the unit vector $\vec{t}^{track}$ is a 3 dimensional vector represented by a 3*1 matrix, and its superscript 'track' represents the unit vector is in the tracking device coordinate system 'track', and the expression of formula for conversion is presented as bellow:

$$\vec{t}^{track} = R_{tool}^{track} \cdot \vec{t}^{tool} \quad (3)$$

In order to allow the imaging device 3 to use the position and orientation data in the tracking device coordinate system 'track', it is required to convert the position and orientation data from the tracking device coordinate system 'track' to the imaging device coordinate system 'scan'. And the conversion module $C_{track}^{scan}$ for conversion between the tracking device coordinate system and the imaging device coordinate system is presented as bellow:

$$C_{track}^{scan} = \begin{pmatrix} R_{track}^{scan} & T_{track}^{scan} \\ 0 & 1 \end{pmatrix} \quad (4)$$

wherein, $C_{track}^{scan}$ is a 4*4 matrix, $R_{track}^{scan}$ is a 3*3 rotation matrix, and $T_{track}^{scan}$ is a 3 dimensional translation vector represented by a 3*1 matrix. The superscript and the subscript of $C_{track}^{scan}$, $R_{track}^{scan}$ and $T_{track}^{scan}$ represent that the position or the orientation of these variables can be converted from the tracking device coordinate system 'track' to the imaging device coordinate system 'scan'. For example, by using the formula below, a coordinate $Q^{track}$ of any point Q in the tracking device coordinate system can be converted into a coordinate $Q^{scan}$ in the imaging device coordinate system 'scan' through a formula presented as bellow:

$$Q^{scan} = C_{track}^{scan} Q^{track} \quad (5)$$

wherein, the coordinate $Q^{track}$ is a 3 dimensional vector represented by a 3*1 matrix, and its superscript 'track' represents the coordinate is in the tracking device coordinate system 'track'.

A certain orientation $\vec{t}$ in the tracking coordinate system 'track' can be represented by a unit vector $\vec{t}^{tool}$ (which is a normalized 3 dimensional vector represented by a 3*1 matrix, and its superscript 'tool' represents that the vector is in the tracking coordinate system 'track', and in the imaging device coordinate system 'scan', the orientation is converted into a unit vector $\vec{t}^{scan}$ (which is a normalized 3 dimensional vector represented by a 3*1 matrix, and its superscript 'scan' represents the unit vector $\vec{t}^{scan}$ is in the imaging device coordinate system 'scan'. The expression of the formula of the conversion is presented as bellow:

$$\vec{t}^{scan} = R_{track}^{scan} \cdot \vec{t}^{track} \quad (6)$$

Conversion module $C_{track}^{scan}$ for conversion between the tracking device coordinate system and the imaging device coordinate system can be preset either in the tracking device 2 or the imaging device 3. The conversion module $C_{track}^{scan}$ is used to convert the position and orientation of the target to be scanned from the tracking device coordinate system 'track' to the imaging device coordinate system 'scan'. When the conversion module $C_{track}^{scan}$ is preset in the tracking device 2, the tracking device 2 will transfer the position and orientation of the target to be scanned to the imaging device 3, and then the imaging device 3 will convert the position and orientation from the tracking device coordinate system to the imaging device coordinate system. The imaging device may conduct scanning in terms of the position and orientation of the target to be scanned in its own coordinate system.

Conversion module $C_{track}^{scan}$ for conversion between the tracking device coordinate system and the imaging device coordinate system can be obtained through other technical calibrations, such as the one disclosed in Chinese patent under no. ZL200710064900.2, titled 'A navigating method and a navigation System for Supporting Multiple Modes'. In this patent, inverse matrix $C_{scan}^{track}$ of conversion module $C_{track}^{scan}$ for conversion between the tracking device coordinate system and the imaging device coordinate system is obtained, and the conversion module $C_{track}^{scan}$ can be obtained through inversion, and the expression of formula of conversion module $C_{track}^{scan}$ is presented as bellow:

$$C_{track}^{scan} = (C_{scan}^{track})^{-1} \quad (7)$$

Figure 4:
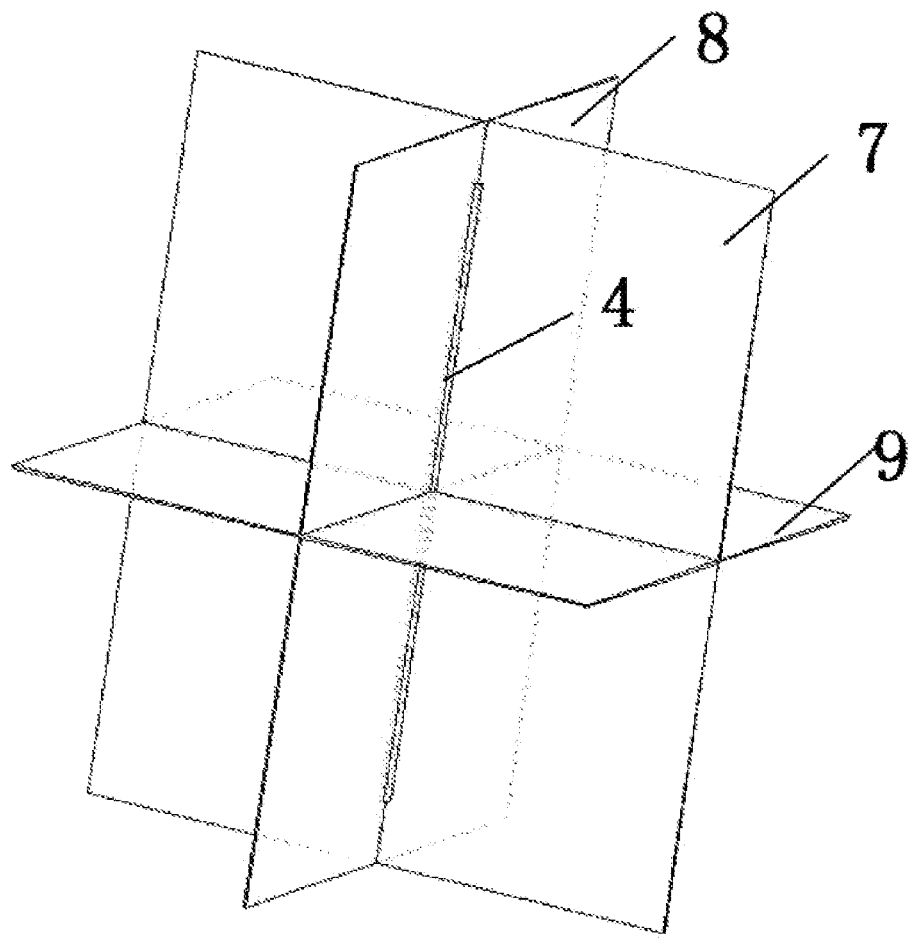
FIG. 4 shows the use of the scanning plane of this invention.

According to FIG. 4, for a needle shaped device 4, there are three types of ordinary scanning planes, for example, plane 7 and plane 8 pass the needle shaped device 4 and are perpendicular to each other, and plane 9 is perpendicular to plane 8 and 7 respectively. The information of the entire image can be quickly provided through observation of the combination of the three planes. In addition, the needle shaped device 4 can be used as a probe, for example, it may scan what it points to, so as to improve the flexibility of operation.

The methods for controlling scanning planes of imaging device comprise steps of:

step 1: building a system comprising a tracer 1, a tracking device 2, and an imaging device 3; and then fixing the tracer on a target to be scanned; and presetting a conversion module for conversion between a tracking device coordinate system and an imaging device coordinate system in a tracking device or an imaging device;

step 2: defining a plane with a certain thickness as a scanning plane G of the imaging device, and an expression of formula of the scanning plane G in the tracer coordinate system is presented as:

$$\vec{n}^{tool} \cdot (X^{tool} - S^{tool}) = 0 \quad (8)$$

wherein, $X^{tool}$ represents a coordinate of any point on plane G in the tracer coordinate system 'tool', which is an unknown 3*1 matrix, and is also an unknown 3D vector; $\vec{n}^{tool}$ represents the normal vector of plane G is in the tracer coordinate system, which is a 3*1 matrix and is also a normalized 3 dimensional vector. $S^{tool}$ represents a coordinate of a known point on plane G in the tracer coordinate system, which is a 3*1 matrix and is also a 3 dimensional vector. The superscript of $X^{tool}$, $\vec{n}^{tool}$ and $S^{tool}$ represents these vectors are in the tracer coordinate system 'tool'. $\vec{n}^{tool}$ and $S^{tool}$ are known vectors and can be obtained through mechanical design and calibration, during the process of designing a tracer 1;

step 3: measuring a position and orientation $C_{tool}^{track}$ of the tracer 1 in the tracking device coordinate system 'track' with the tracking device 2, wherein, $C_{tool}^{track}$ is a conversion matrix for conversion from the tracer coordinate system 'tool' to the tracking device coordinate system 'track', and an expression of formula 1 of the conversion matrix is presented as bellow:

$$C_{tool}^{track} = \begin{pmatrix} R_{tool}^{track} & T_{tool}^{track} \\ 0 & 1 \end{pmatrix} \quad (1)$$

step 4: calculating a first plane equation of scanning plane G in the tracking device coordinate system 'track' with the tracking device using the position and orientation $C_{tool}^{track}$ of formula 1, which is the position and orientation of the tracer 1 in the tracking device coordinate system 'track', together with formulas 2, 3, and 8, and an expression of the first plane equation is presented as bellow:

$$\vec{n}^{track} \cdot (X^{track} - S^{track}) = 0 \quad (9)$$

$$\vec{n}^{track} = R_{tool}^{track} \cdot \vec{n}^{tool} \quad (10)$$

$$S^{track} = R_{tool}^{track} \cdot S^{tool} + T_{tool}^{track} \quad (11)$$

wherein, a normal vector of the scanning plane G in the tracking device coordinate system 'track' is represented by $\vec{n}^{track}$, which is a 3*1 matrix, and is also a normalized 3 dimensional vector. Its superscript 'track' represents that the vector is in the tracking device coordinate system 'track'; $X^{track}$ represents the coordinate of any point on the scanning plane G in the tracking device coordinate system 'track', which is an unknown 3*1 matrix and is also an unknown 3 dimensional vector. Its superscript 'track' represents that its vector is in the tracking device coordinate system 'track'; $S^{track}$ represents the coordinate of a known point on the scanning plane G in the tracking device coordinate system, which is a 3*1 matrix and is also a 3 dimensional vector, and its superscript 'track' represents the vector is in the tracking device coordinate system 'track';

step 5: calculating a second plane equation of scanning plane G in the imaging device coordinate system 'scan' with the tracking device 2 using the conversion module $C_{track}^{scan}$ for conversion between the tracking device coordinate system and the imaging device coordinate system in formula 4 and with formula 5, 6, 9, 10, and 11, an expression of the second plane equation is presented as bellow:

$$\vec{n}^{scan} \cdot (X^{scan} - S^{scan}) = 0 \quad (12)$$

$$\vec{n}^{scan} = R_{track}^{scan} \cdot \vec{n}^{track} = R_{track}^{scan} \cdot R_{tool}^{track} \cdot \vec{n}^{tool} \quad (13)$$

$$S^{scan} = R_{track}^{scan} \cdot S^{track} + T_{track}^{scan} = R_{track}^{scan} \cdot (R_{tool}^{track} \cdot S^{tool} + T_{tool}^{track}) + T_{track}^{scan} \quad (14)$$

wherein, $\vec{n}^{scan}$ represents a normal vector of the scanning plane G in the imaging device coordinate system 'scan', which is a 3*1 matrix and is also a normalized 3 dimensional vector. Its superscript 'scan' represents the vector is in imaging device coordinate system 'scan'; $X^{scan}$ represent a coordinate of any point on said scanning plane G in said imaging device coordinate system, which is a unknown 3*1 matrix and is also a unknown 3 dimensional vector and its superscript 'scan' represents the vector is in the imaging device coordinate system 'scan'; $S^{scan}$ represents a coordinate of a known point on the scanning plane G in the imaging device coordinate system, which is a 3*1 matrix and is also a 3 dimensional vector; its superscript 'scan' represents its unit vector is in imaging device coordinate system 'scan'. After the plane equations 12, 13, and 14 of the scanning plane G in the imaging device coordinate system 'scan' are calculated, tracking device (2) will transfer these equations to the imaging device 3;

step 6: scanning the target to be scanned with the imaging device 3, in terms of the plane equations 12, 13 and 14 of the scanning plane G in the imaging device coordinate system 'scan'.

Referring to the step 5 mentioned above, it is also possible to transfer the plane equations 9, 10, and 11 of the scanning plane G in the tracking device coordinate system from the tracking device 2 to the imaging device 3, and then the imaging device 3 calculates plane equations 12, 13, and 14 of the scanning plane G in the imaging device coordinate system 'scan'.

What is claimed is:

1. A system for controlling scanning planes of imaging device, comprising:
    a tracer, on which a tracer coordinate system is built, fixed on a target which is to be scanned;
    a tracking device, on which a tracking device coordinate system is built, for obtaining the position and orientation of the tracer in said tracking device coordinate system and converting the known position and orientation of the target to be scanned from a coordinate system of said tracer to a coordinate system of said tracking device; and
    an imaging device, for scanning the position and orientation of the target to be scanned in said coordinate system of said imaging device to form images, on which an imaging device coordinate system is built;
    wherein, said tracking device or said imaging device has a conversion module preset therein, which is for converting the position and orientation of the target to be scanned from the tracking device coordinate system to the imaging device coordinate system; and when the conversion module is preset in the tracking device, the tracking device transfers the position and orientation of the target to be scanned in the tracking device coordinate system to the imaging device;
    and a way of implementation of said system comprises
    step 1: building a system comprising a tracer, a tracking device, and an imaging device; and then fixing said tracer a target to be scanned; and, presetting a conversion module for conversion between a tracking device coordinate system and an imaging device coordinate system in a tracking device or a imaging device;
    step 2: defining a plane through which said imaging device scans a target to be scanned as a scanning plane G, and an expression of formula of said scanning plane G in said tracer coordinate system is presented as:

$$\vec{n}^{tool} \cdot (X^{tool} - S^{tool}) = 0$$

wherein, $X^{tool}$ represents a coordinate of any point on said scanning plane G in said tracer coordinate system 'tool', which is 3 dimensional vector; $\vec{n}^{tool}$ represents a normal vector of said scanning plane G in the tracer coordinate system, which is a normalized 3 dimensional vector; $S^{tool}$ represents a coordinate of a known point on said scanning plane G in the tracer coordinate system, which is 3 dimensional vector;
    step 3: measuring a position and orientation $C_{tool}^{track}$ of said tracer 1 in said tracking device coordinate system 'track' with said tracking device 2;
    Step 4: calculating a first plane equation of scanning plane G in the tracking device coordinate system with the tracking device using the position and orientation $C_{tool}^{track}$ of step 3, wherein, an expression of said first plane equation is presented as bellow:

$$\vec{n}^{track} \cdot (X^{track} - S^{track}) = 0$$

$$\vec{n}^{track} = R_{tool}^{track} \cdot \vec{n}^{tool}$$

$$S^{track} = R_{tool}^{track} \cdot S^{tool} + T_{tool}^{track}$$

in which $\vec{n}^{track}$ represents a normal vector of said scanning plane G in said tracking device coordinate system, which is a normalized 3 dimensional vector; $X^{track}$ represents a coordinate of any point on said scanning plane G in said tracking device coordinate system, which is a 3 dimensional vector; and $S^{track}$ represents a coordinate of a known point on said scanning plane G in said tracking device coordinate system, which is a 3 dimensional vector;
    step 5: calculating a second plane equation of said scanning plane G in said imaging device coordinate system in terms of a conversion module $C_{track}^{scan}$ for conversion between said tracking device coordinate system and said imaging device coordinate system, wherein, an expression of said second plane equation is presented as bellow:

$$\vec{n}^{scan} \cdot (X^{scan} - S^{scan}) = 0$$

$$\vec{n}^{scan} = R_{track}^{scan} \cdot \vec{n}^{track} = R_{track}^{scan} \cdot R_{tool}^{track} \cdot \vec{n}^{tool}$$

$$S^{scan} = R_{track}^{scan} \cdot S^{track} + T_{track}^{scan} = R_{track}^{scan} \cdot (R_{tool}^{track} \cdot S^{tool} + T_{tool}^{track}) + T_{track}^{scan}$$

in which $\vec{n}^{scan}$ represents a normal vector of said scanning plane G in said imaging device coordinate system, which is a normalized 3 dimensional vector; $X^{scan}$ represent a coordinate of any point on said scanning plane G in said imaging device coordinate system, which is a 3 dimensional vector; $S^{scan}$ represents a coordinate of a known point on said scanning plane G in the imaging device coordinate system, which is a 3 dimensional vector; and
    Step 6: scanning said target to be scanned with said imaging device 3, in terms of said second plane equation calculated in step 5.

2. The system of claim 1, wherein, the expression of said conversion module $C_{track}^{scan}$ is presented as:

$$C_{track}^{scan} = \begin{pmatrix} R_{track}^{scan} & T_{track}^{scan} \\ 0 & 1 \end{pmatrix}$$

$C_{track}^{scan}$ is a 4*4 matrix, $R_{track}^{scan}$ is a 3*3 rotation matrix, and $T_{track}^{scan}$ is a 3 dimensional translation vector.

3. The system of claim 2, wherein, said tracer comprises
    a position/orientation sensor and a fixing support;
    a position/orientation sensor is fixed via said fixing support on said target to be scanned; and
    a position and orientation of said position/orientation sensor is the same as a position and orientation of said tracer.

4. The system of claim 1, wherein, said tracer comprises
    a position/orientation sensor and a fixing support;
    a position/orientation sensor is fixed via said fixing support on said target to be scanned; and
    a position and orientation of said position/orientation sensor is the same as a position and orientation of said tracer.

5. The system of any one of claim 1-4, wherein,
    an expression of said position and orientation $C_{tool}^{track}$ of said tracer in said tracking device coordinate system is presented as:

$$C_{tool}^{track} = \begin{pmatrix} R_{tool}^{track} & T_{tool}^{track} \\ 0 & 1 \end{pmatrix}$$

and $C_{tool}^{track}$ is a 4*4 matrix, $R_{track}^{scan}$ is a 3*3 rotation matrix, and $T_{track}^{scan}$ is a 3 dimensional translation vector.

6. A method for controlling scanning planes of imaging device comprise steps of
- step 1: building a system comprising a tracer, a tracking device, and an imaging device; and then fixing said tracer a target to be scanned; and, presetting a conversion module for conversion between a tracking device coordinate system and an imaging device coordinate system in a tracking device or a imaging device;
- step 2: defining a plane through which said imaging device scans a target to be scanned as a scanning plane G, and an expression of formula of said scanning plane G in said tracer coordinate system is presented as:

$$\vec{n}^{tool} \cdot (X^{tool} - S^{tool}) = 0$$

wherein, $X^{tool}$ represents a coordinate of any point on said scanning plane G in said tracer coordinate system 'tool', which is 3 dimensional vector; $\vec{n}^{tool}$ represents a normal vector of said scanning plane G in the tracer coordinate system, which is a normalized 3 dimensional vector; $S^{tool}$ represents a coordinate of a known point on said scanning plane G in the tracer coordinate system, which is 3 dimensional vector;

- step 3: measuring a position and orientation $C_{tool}^{track}$ of said tracer 1 in said tracking device coordinate system 'track' with said tracking device 2;
- Step 4: calculating a first plane equation of scanning plane G in the tracking device coordinate system with the tracking device using the position and orientation $C_{tool}^{track}$ of step 3, wherein, an expression of said first plane equation is presented as bellow:

$$\vec{n}^{track} \cdot (X^{track} - S^{track}) = 0$$

$$\vec{n}^{track} = R_{tool}^{track} \cdot \vec{n}^{tool}$$

$$S^{track} = R_{tool}^{track} \cdot S^{tool} + T_{tool}^{track}$$

in which $\vec{n}^{track}$ represents a normal vector of said scanning plane G in said tracking device coordinate system, which is a normalized 3 dimensional vector; $X^{track}$ represents a coordinate of any point on said scanning plane G in said tracking device coordinate system, which is a 3 dimensional vector; and $S^{track}$ represent a coordinate of a known point on said scanning plane G in said tracking device coordinate system, which is a 3 dimensional vector;

- step 5: calculating a second plane equation of said scanning plane G in said imaging device coordinate system in terms of a conversion module $C_{track}^{scan}$ for conversion between said tracking device coordinate system and said imaging device coordinate system, wherein, an expression of said second plane equation is presented as bellow:

$$\vec{n}^{scan} \cdot (X^{scan} - S^{scan}) = 0$$

$$\vec{n}^{scan} = R_{track}^{scan} \cdot \vec{n}^{track} = R_{track}^{scan} \cdot R_{tool}^{track} \cdot \vec{n}^{tool}$$

$$S^{scan} = R_{track}^{scan} \cdot S^{track} + T_{track}^{scan} = R_{track}^{scan} \cdot (R_{tool}^{track} \cdot S^{tool} + T_{tool}^{track}) + T_{track}^{scan}$$

in which $\vec{n}^{scan}$ represents a normal vector of said scanning plane G in said imaging device coordinate system, which is a normalized 3 dimensional vector; $X^{scan}$ represent a coordinate of any point on said scanning plane G in said imaging device coordinate system, which is a 3 dimensional vector; $S^{scan}$ represents a coordinate of a known point on said scanning plane G in the imaging device coordinate system, which is a 3 dimensional vector; and Step 6: scanning said target to be scanned with said imaging device 3, in terms of said second plane equation calculated in step 5.

7. The method of claim 6, wherein, an expression of said conversion matrix $C_{track}^{scan}$ in step 1 is $$C_{track}^{scan} = \begin{pmatrix} R_{track}^{scan} & T_{track}^{scan} \\ 0 & 1 \end{pmatrix}$$

and $C_{track}^{scan}$ is a 4*4 matrix, $R_{track}^{scan}$ is a 3*3 rotation matrix, and $T_{track}^{scan}$ is a 3 dimensional translation vector.

8. The method of claim 7, wherein, an expression of said position and orientation $C_{tool}^{track}$ in step 3 is $$C_{tool}^{track} = \begin{pmatrix} R_{tool}^{track} & T_{tool}^{track} \\ 0 & 1 \end{pmatrix}$$

$C_{tool}^{track}$ is a 4*4 matrix, $R_{tool}^{track}$ is a 3*3 matrix, and $T_{tool}^{track}$ is a 3 dimensional translation vector.

9. The method of claim 6 or 7, wherein, if said conversion module is preset in said tracking device, said second plane equation of said scanning plane G in said imaging device coordinate system may be calculated by said tracking device and then transferred to said imaging device.

10. The method of claim 6 or 7, wherein, if said conversion module is preset in said imaging device, said second plane equation of said scanning plane G in said imaging device coordinate system may be calculated by said imaging device.

* * * * *